United States Patent [19]

Duvillier et al.

[11] Patent Number: 5,749,876
[45] Date of Patent: May 12, 1998

[54] APPARATUS FOR RESECTION OF THE CONDYLES OF THE KNEE FOR PUTTING A PROSTHESIS INTO PLACE, AND METHOD FOR PUTTING SUCH AN APPARATUS INTO POSITION

[75] Inventors: Eric Duvillier, Paris; Jean-Marie Gineston, Neuilly; Olivier De Roaldes, Longpont-Sur-Orge, all of France

[73] Assignees: Biomicron, Clichy; Ortho Diffusion & Recherche, Caen, both of France

[21] Appl. No.: 612,917
[22] PCT Filed: Jul. 11, 1995
[86] PCT No.: PCT/FR95/00923
§ 371 Date: Apr. 23, 1996
§ 102(e) Date: Apr. 23, 1996
[87] PCT Pub. No.: WO96/01588
PCT Pub. Date: Jul. 25, 1996

[30] Foreign Application Priority Data

Jul. 12, 1994 [FR] France .................. 94 08670

[51] Int. Cl.⁶ .................. A61B 17/15
[52] U.S. Cl. .................. 606/88; 606/86; 606/89
[58] Field of Search .................. 606/86, 87, 88, 606/89

[56] References Cited

U.S. PATENT DOCUMENTS 4,892,093   1/1990   Zarnowski et al. .......... 606/82
5,474,559  12/1995   Bertin et al. .............. 606/89

FOREIGN PATENT DOCUMENTS

| 0 538 153 | 4/1993 | European Pat. Off. |
| 0 555 003 | 8/1993 | European Pat. Off. |
| 2 664 157 | 1/1992 | France |
| 2 679 766 | 2/1993 | France |
| 2 681 779 | 4/1993 | France |

Primary Examiner—Michael Buiz
Assistant Examiner—David O. Reip
Attorney, Agent, or Firm—Merchant, Gould, Smith, Edell, Welter & Schmidt, P.A.

[57] ABSTRACT

Apparatus for resectioning knee condyles, enabling a prosthesis to be fitted, comprising a femoral cutting device (12) comprising a support element (14), a femoral cutting blade guide (21, 24, 30) fixed and vertically adjustable in relation to the support element, a femoral intramedullary rod (28) for orienting and centering said device and feeler means (56, 57, 78) for the anterior cortical femur portion (58, 79). The cutting blade guide includes at least two blocks (21, 24, 30) movable in relation to the support element and vertically adjustable in relation to the support element and vertically adjustable in relation to one another. One of the blocks comprises means for guiding at least one anterior, posterior, anterior chamfer or posterior chamfer cut, the block also having means for guiding the remaining cutting operations.

18 Claims, 10 Drawing Sheets

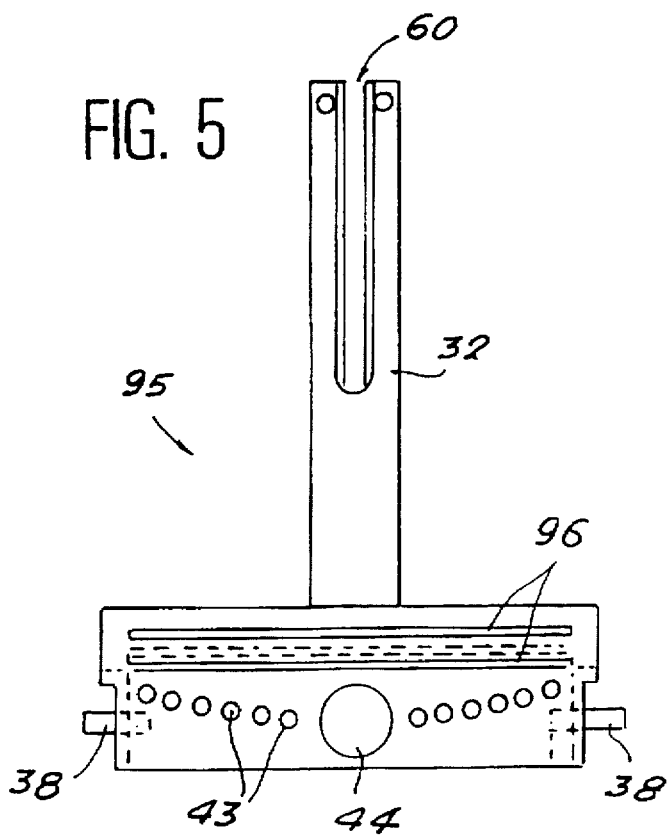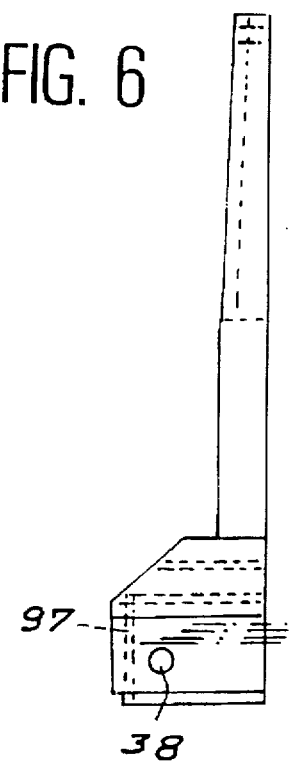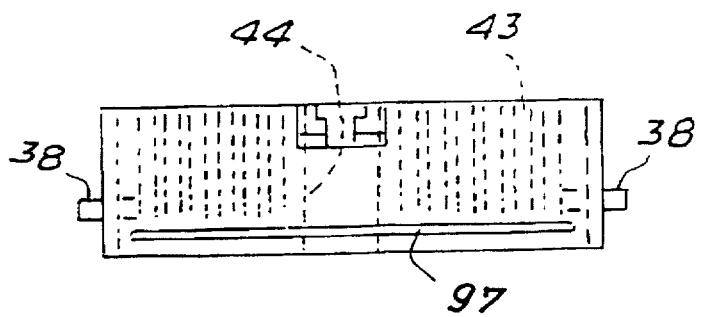

APPARATUS FOR RESECTION OF THE CONDYLES OF THE KNEE FOR PUTTING A PROSTHESIS INTO PLACE, AND METHOD FOR PUTTING SUCH AN APPARATUS INTO POSITION

The present invention relates to an apparatus for resection of the condyles of the knee for putting a prosthesis into place, comprising a femoral cutting device of the type including a support element equipped with a lower baseplate able to cooperate, in a bearing manner, with the femoral condyles, a guide for blades for femoral cuts, called anterior cut, beveled anterior cut, beveled posterior cut, posterior cut and distal cut, the guide being fixed to the support element and comprising at least one block which is adjustable in height in relation to said support element, an intramedullary femoral rod for orientation and centering of the device, and means for tracing the anterior cortical portion of the femur, said means being integral with the guide.

The invention also relates to a method for putting such an apparatus into position.

It has a particularly important, although not exclusive, application in the field of knee arthroplasty, the aim of which is to restore the articular function of the knee whose condylar surfaces have been progressively damaged as a result of arthrosis.

It is known that arthroplasty affords good results only if the prostheses are put into place with precision, which necessitates an ancillary preparation apparatus permitting, on the one hand, an exact orientation of the cutting guides in order to reproduce the mechanical alignment of the lower limb being treated, and, on the other hand, a balance between the cuts on the tibial and femoral articular surfaces in order to obtain a good stability over the whole area of the knee joint.

To do this, it is necessary that the prosthesis respect precisely the mechanical axis 1 of the lower limb being treated (see FIG. 1), which axis passes through the center 2 of the femoral head 3, through the center 4 of the knee joint 5, and through the center 6 of the ankle joint 7.

Now, the mechanical axis 1 forms, together with the anatomical axis 8 of the femur 9, an angle of between 3° and 90°, depending on the individual, and is in contrast substantially superposed with the anatomical axis 10 of the tibia 11, except in the case of deformation.

The correct orientation of the resecting apparatus, and its positioning in a simple and reliable manner as a function of the different axes, is thus of paramount importance to the practitioner.

A large number of ancillary apparatuses for femoral and/or tibial cutting are already known.

The document FR A 2,679,766 describes, for example, a femoral cutting device which permits a correct positioning of the prosthetic implants in the frontal and sagittal planes.

However, such a device has disadvantages.

This is because it requires several guides for cutting blades of different dimensions in order to adapt to the different joint sizes. This results in the risk of mistakes during the positioning of the guide, this positioning in most cases being preselected by trial and error. Furthermore, a long time is taken in putting the guide into position, and the cost and the size of the components of the device taken as a whole are also considerable.

A resecting apparatus is also known (FR-A-2,664,157) which includes a cutting blade guide in two blocks, namely a first block integral with the support element for the beveled cuts and the posterior cut, and a second block which is adjustable in height in relation to the first one in order to effect the anterior cut.

Here, once again, such an apparatus presents disadvantages associated with its lack of adaptability to the dimensions of the patient's condyles.

The document FR 2,629,339 describes for its part installation equipment for a tibial element, comprising an external guide rod integral with the tibial cutting guide and designed to be fixed temporarily on a portion of the tibia.

Such equipment also has disadvantages. It is not in fact very reliable because it is difficult to control and has a tendency to produce a cut which is not perfectly orthogonal to the anatomical axis of the tibia.

Installation apparatuses for a tibial element are also known which comprise an intramedullary positioning rod.

Such apparatuses are not entirely satisfactory either, since they do not allow for the possibility of modifying the alignment of the cutting guide, for example in order to make good an initial error in the intramedullary centering of the rod or a deformation.

In an attempt to remedy these disadvantages, the document FR-A-2,681,779 proposes an ancillary apparatus comprising an intramedullary rod and an external sighting rod allowing the practitioner to perform two types of sightings.

However, such an apparatus does not allow the cutting guide to adapt perfectly to the condyle of the knee to be cut.

The object of the present invention is to make available an apparatus for resection of the condyles of the knee for putting a prosthesis into place, this apparatus responding more effectively than those of the prior art to the practical requirements, particularly in that it makes it possible to use only one guide for blades for femoral cuts, whatever the size of the femurs to be treated, in that it uses a tibial cutting device which is articulated in the frontal and sagittal plane, and in that it can be put into use easily and quickly by the practitioner, while guaranteeing correct and reliable positioning of the cutting guides.

The invention also makes it possible to choose, as a constant indicator for the femoral cuts, either the bicondylar plane or the plane of the anterior cortical portion of the femur, which therefore makes it possible to avoid ligament imbalances by virtue of a greater adaptability to the type of femur encountered.

To this end, the invention proposes in particular an apparatus for resection of the condyles of the knee for putting a prosthesis into place, comprising a femoral cutting device of the type which is defined hereinabove, characterized in that the cutting blade guide includes at least three blocks, of which at least two blocks are movable in relation to said support element, said blocks being adjustable in height in relation to one another, one of the blocks comprising means for guiding at least one cut from among the anterior cut, posterior cut, beveled anterior cut, and beveled posterior cut, and the other blocks comprising means for guiding the remaining cuts from among said anterior cut, posterior cut, beveled anterior cut and beveled posterior cut.

In advantageous embodiments, recourse is also had to one or other of the following arrangements:

the three blocks are movable in relation to said support element and comprise a lower block for the posterior cut, a central block for the beveled anterior and beveled posterior cuts, and an upper block for the anterior cut;

the cutting blade guide includes four blocks which are movable in relation to said support element, namely a lower block for the posterior cut, two median blocks comprising a first median block for the beveled anterior cut and a second median block for the beveled posterior cut, and an upper block for the anterior cut;

the femoral cutting device includes means for adjusting the spacings between blocks in a proportional manner;

the means for adjusting the spacings between blocks in a proportional manner comprise two lateral flanges which are disposed on either side of the blocks and are movable in rotation about a central shaft between two positions, namely a position in which the blocks are spaced apart to the maximum from one another, and a position in which the blocks are brought together, said lateral flanges being equipped with slots in the shape of an arc of a circle, able to cooperate with spindles which are integral with the outer lateral walls of the movable blocks between them;

the cutting blade guide including a central block for the beveled cuts, the central shaft is integral with said central block and the lateral flanges are each equipped with two slots in the shape of an arc of a circle or a curve, which are symmetrical in relation to said central shaft and are able to cooperate with spindles respectively integral with the lateral walls of the lower and upper blocks;

the cutting blade guide including two median blocks, the central shaft is integral with one or two intermediate elements disposed between the two median blocks, and the lateral flanges are each equipped with four slots in the shape of an arc of a circle and symmetrical in pairs in relation to said central shaft, namely two outer slots able to cooperate with spindles respectively integral with the lateral walls of the lower and upper blocks, and two inner slots able to cooperate with spindles respectively integral with the lateral walls of the median blocks;

the slots of said lateral flanges are notched internally, the notches being able to cooperate with said spindles by catching;

the upper peripheral edge of the flanges is curved, notched, with the same curve shape as the slots, the adjustment means comprising a component in the form of an angle bracket equipped with two lateral end parts whose respective peripheral edges include a lip which is able to cooperate with the notches, said component being tiltable and movable in rotation about an axis integral with the upper block, between a compressed position, in which the lips are freed from the notches, and a spring-return position, in which the lips are caught in said notches;

the lower baseplate of the support element comprises at least one movable plate which is able to cooperate, in a bearing manner, with the femoral condyles;

the lower block is adjustable in height in relation to the lower baseplate by a distance smaller than or equal to a defined value;

the support element includes two pairs of columns which guide the blocks, connected to one another by end-pieces and situated on either side of the apparatus, said blocks comprising bores for the passage of said columns in order to allow said blocks to slide with slight friction along said columns between the two said positions;

the means for tracing the anterior cortical portion of the femur can be displaced laterally in relation to the support element;

the femoral cutting device includes means for adjusting the angle formed between the axis perpendicular to the cutting blade guide and the intramedullary rod;

the means for adjusting the angle are integral with the femoral intramedullary rod;

the means for adjusting the angle are integral with the upper block;

the cutting blade guide includes a distal cutting block integral with the anterior cutting block and equipped with at least two slits for guiding the distal cutting blades;

the apparatus includes a tibial cutting device equipped with a centering component which is able to cooperate with a tibial intramedullary rod, said tibial cutting device including a rod external to the tibia, one end of which rod is integral with said component and includes a cutting block equipped with a curved surface for contact with the tibia, and the other end of which rod is designed to be fixed temporarily on a portion of the tibia;

the rod external to the tibia and integral with the centering component is fixed to said component via an intermediate element designed to permit an adjustment of the position of the tibial cutting block in the frontal plane and in the sagittal plane, by pivoting about a center coinciding with the center of gravity, or substantially with the center of gravity, of said tibial cutting guide;

the intermediate element comprises an open-worked component in the form of a cylindrical tube portion defining a slot in which the end of the external rod can be displaced, said end being equipped with two hemispherical wedges situated on either side of said component, said wedges being able to cooperate with friction and to be held pressed against the inner and outer cylindrical surfaces of said component by clamping means, the center of the hemispherical wedges and the axis of the cylinder passing through the center, or substantially the center, of gravity or of geometry of said cutting block.

The invention also proposes a method in which a support element is put into position bearing on the femoral condyles, the femur being in the flexed position, a femoral intramedullary rod is introduced into the femur for orientation and centering of a guide for femoral cutting blades which is integral with said rod, and fixed to the support element with which it is adjustable in height, then, once the orientation of the blade guide has been adjusted to take account of the angle existing between the mechanical axis of the lower limb and the anatomical axis of the femur, the support element is fixed to the femur, and the intramedullary rod is withdrawn, characterized in that the spacings between the cutting blade guides are then adjusted in a proportional manner, namely the spacing between the blade guide for the anterior cut and the blade guides for the beveled anterior and beveled posterior cuts on the one hand, and between said blade guides for the beveled anterior and beveled posterior cuts and the blade guide for the posterior cut, on the other hand.

Such adjustment is advantageously carried out simultaneously.

Again advantageously, the method is characterized in that a tibial intramedullary rod is moreover introduced into the tibia, and the positioning of a tibial cutting guide is adjusted in the horizontal and sagittal plane via an external correcting rod.

The invention will be better understood from reading the following description of embodiments given by way of nonlimiting example.

In the description, reference is made to the drawings which accompany it, and in which:

FIG. 1, which has already been described, is a front elevation of the skeletal makeup of the lower limb in humans.

FIG. 2a is a diagrammatic perspective view of an alternative embodiment of the means for adjusting the distance between blocks, according to the invention.

FIGS. 5 to 7 are plan, side and front views, respectively, of the upper block of the guide for femoral cutting blades according to another embodiment of the invention, permitting the rotational adjustment of the femoral cutting guide in order to compensate for the angle differential between anatomical axis and mechanical axis.

According to the invention, the apparatus for resection of the condyles of the knee for putting a prosthesis (not shown) into place comprises a femoral cutting device and a tibial cutting device.

Figure 2:
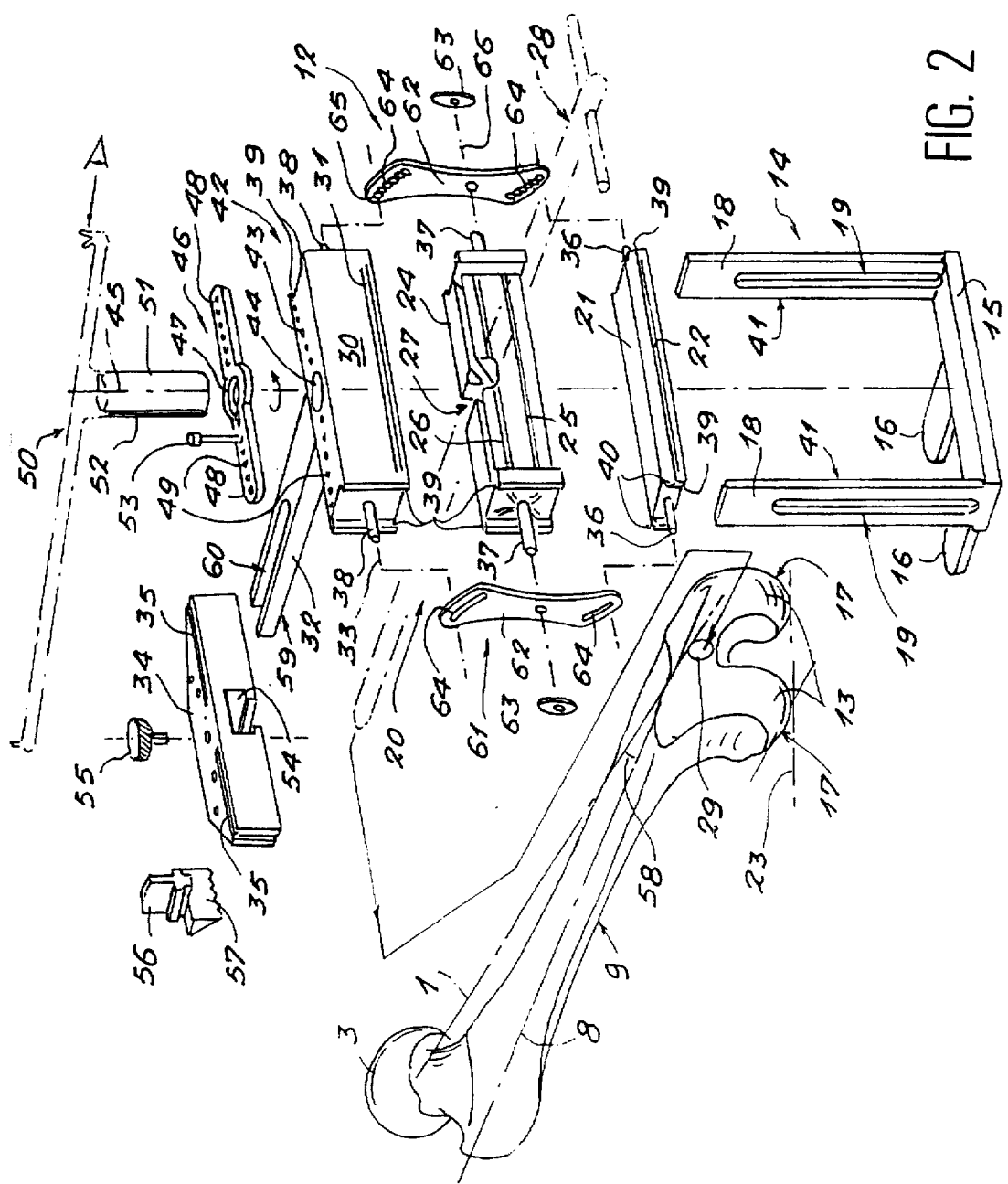
FIG. 2 is a perspective and exploded view of an embodiment of the femoral cutting device belonging to an apparatus according to the invention, designed to cooperate with a femur in the flexed position.
Figure 1:
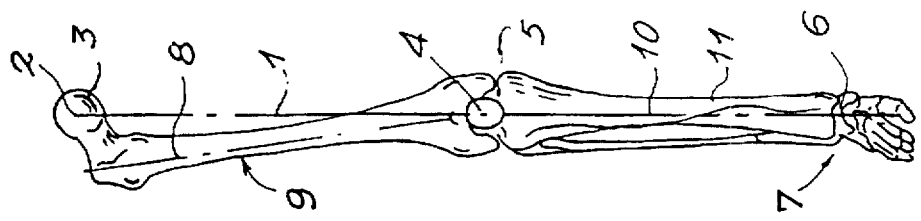
Figure 2:
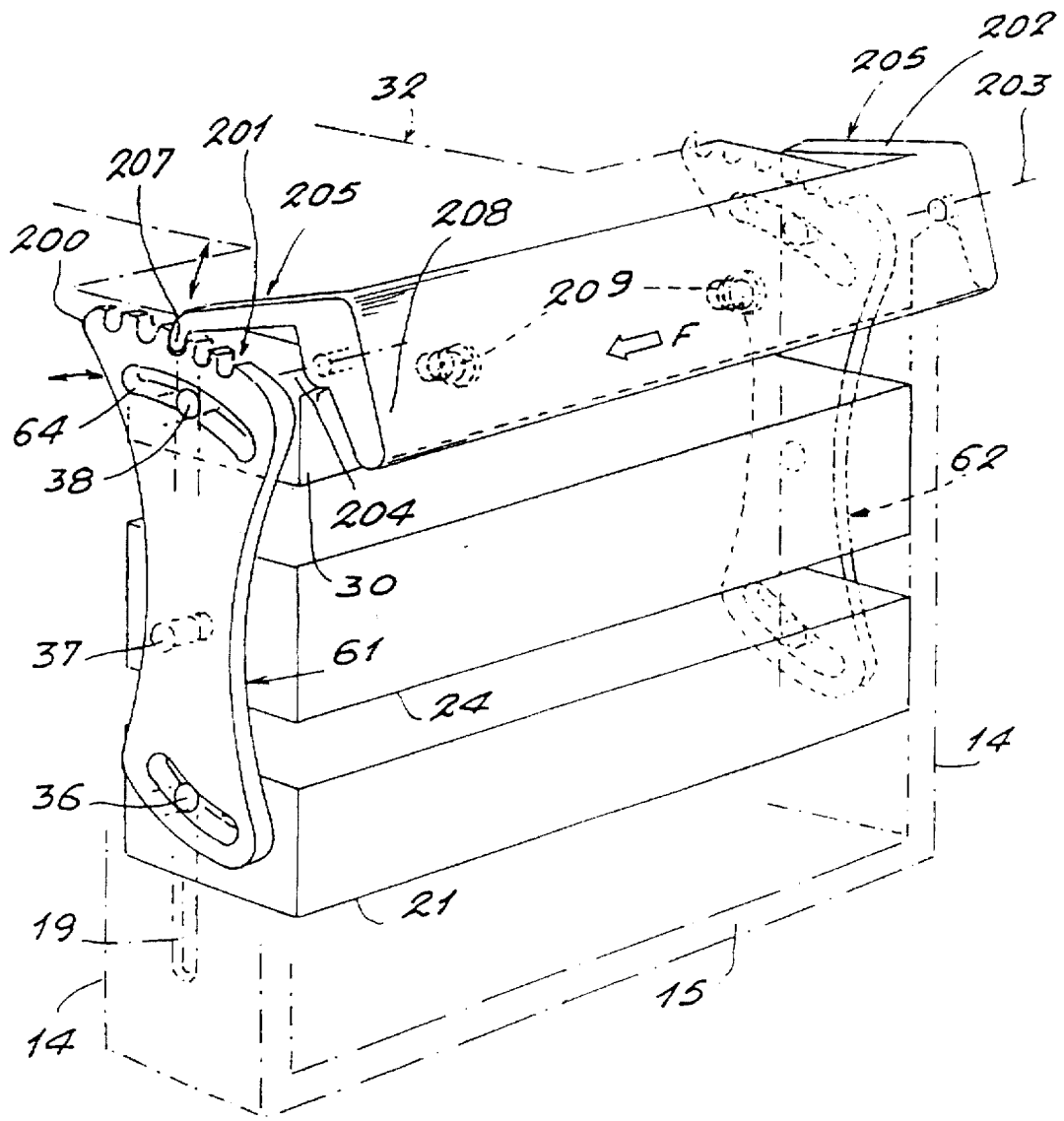

FIG. 2 shows in a perspective and exploded view a femoral cutting device 12, made of stainless steel, able to cut the condyles 13 of the femur 9 in FIG. 1, according to a first embodiment.

The device 12 comprises a support element 14 including a lower baseplate in the form of a rectangular plate 15 equipped on one side with two lateral tongues 16 which are perpendicular to the baseplate, flat and symmetrical, and each able to cooperate, in a bearing manner, with the lower surface 17 of a condyle 13.

The support element 14 comprises two vertical and lateral uprights 18, in the form of an elongate plate, each equipped with a longitudinal slot 19 over most of its height.

The device 12 additionally includes a guide 20 for femoral cutting blades (not shown) comprising three solid steel blocks which are movable in the vertical direction, on the one hand in relation to the support element 14 and on the other hand in relation to one another.

These are, in the first instance, a lower, parallelepipedal block 21 equipped with a slit 22 passing transversely right through the block, substantially parallel to the lateral tongues 16 and designed to effect a horizontal cut of the lower part of the condyles, called a posterior cut, parallel to the posterior condylar line 23 (the femur being as usual placed in a decubitus position on the operating table).

Next there is a central parallelepipedal block 24 which is in one piece and of substantially square cross section, comprising two longitudinal slits 25 and 26 passing transversely right through the block, from the bottom upward in one case (25) and from the top downward in the other case (26), forming with one another an angle of 90°, said slits being designed to allow the passage of cutting blades able to form the cuts in the condyles called the beveled posterior cut in the case of the slit 26 and the beveled anterior cut in the case of the slit 25.

The block 24 furthermore comprises a conical orifice 27 for transverse passage of an intramedullary rod 28 (in dot-and-dash lines in FIG. 2) through the block, for orientation and centering of the device.

The conical orifice 27 permits an angular displacement of the overall device about the axis of the rod 28, in order to compensate for the angle existing between the axes 1 and 8 of the femur.

The rod 28 for its part is introduced into the medullary canal of the femur, centered about the anatomical axis 8 of the latter, via an orifice 29 previously drilled at the center of the joint.

Finally, the device 12 comprises an upper, parallelepipedal block 30 equipped with a slit 31 substantially parallel to the slit 22 of the block 21, passing transversely right through the block 30 and designed to effect a horizontal or substantially horizontal cut, inclined slightly upward, for example by 30° (Morse cone), and called the anterior cut, in the upper part of the condyles of the femur in a decubitus position.

The block 30 is moreover equipped with a lateral rod 32 which is perpendicular to the longitudinal axis 33 of the block 30 and centered in relation to said block.

The rod 32 supports a fourth movable block 34 for a vertical cut of the condyles, called the distal cut, perpendicular to the mechanical axis 1 of the femur.

The block 34 comprises two symmetrical vertical slits 35 which are situated on either side of the block and which pass right through the ends of said block over a longitudinal distance corresponding to the width of the two condylar ends.

The blocks 21, 24 and 30 moreover comprise, on each of their transverse lateral faces, a cylindrical axial pin, namely pins 36, 37 and 38 respectively, able to cooperate in a sliding manner with the slot 19 of the upright 18 opposite, which slot thus serves as a vertical guide rail on either side of said blocks.

Lateral projecting flanges 39, continuing the longitudinal vertical faces of each block, and situated on either side of the latter, and whose inner faces 40 constitute friction surfaces intended to interact with the vertical lateral edges 41 of the corresponding upright 18, complete the guiding by preventing the blocks from tilting forward or backward.

The blocks 21, 24 and 30 are of the same width and of the same length. They thus present one face to the condyles of the femur in one and the same plane.

Taking into consideration the angle existing between the anatomical axis 8 of the femur, which coincides with that of the rod 28 when it is introduced therein, and the mechanical axis 1, means 42 for angular adjustment of the position of the overall device 12 in relation to the rod 28 are furthermore provided.

The means 42 include vertical bores 43 of small diameters which are drilled in the block 30. The bores 43 are distributed in two diverging lines starting from a central cylindrical bore 44, of greater diameter, which is vertical and lies about the axis 45 of the device.

The lines form with the shaft 38 of the block 30, respectively and on either side of the bore 44, an angle equal to 10°, for example.

The means 42 also comprise a plate 46 equipped with a central part including an axial orifice 47 and two end tabs 48, as continuations of one another, drilled right through with small cylindrical bores 49, of diameters equal to those of the bores 43, and distributed on an axial line of the plate.

The plate 46 is designed to rest on the upper face of the block 30, the axial orifice 47 then being centered in relation to the bore 44 of the block 30.

The device 12 additionally includes a system 50, which is known per se, for sighting the center of the femoral head, and able to determine the mechanical axis 1.

The system 50 is integral in terms of rotation with the plate 46 and comprises a rod 51 with key 52, able to cooperate with a lateral recess of the orifice 47 facing it (not shown).

A small pin 53 designed to be introduced into the small bores 43 and 49 facing each other permits the blocks to be positioned, and in particular the distal cutting block 34, integral with the block 30, in such a way that the distal cut is perpendicular to the mechanical axis 1 defined by virtue of the sighting system 50.

The block 34 furthermore comprises, on its lower face, a central transverse recess 54, said recess being able to cooperate frictionally with the rod 32 along which the block is displaced and to which it can be fixed by a knurled compression wheel 55.

A cursor 56 equipped with a tracer blade 57 for the anterior cortical portion 58 of the femur is moreover provided to slide along the end 59 of the rod 32, in a guide groove 60.

The cursor 56 is otherwise integral with the rod 32 on the two remaining degrees of freedom.

Such an arrangement allows the position of the device to be adapted as a function of the dimension of the condyles, the end 59 presenting a slight incline directed toward the block 30.

The device 12 furthermore comprises means 61 for adjusting the spacings between blocks in a proportional manner.

The means 61 comprise two lateral flanges 62 in the form of a plate equipped with a central part of smaller width than its end parts.

The flanges are mounted in rotation about pins 37 on either side of the block 24. They are fixed longitudinally by lateral locking nuts 63 and each comprise respectively, on their end part, slots 64 in the shape of an arc of a circle, or curved, which are equipped with inner notches 65 of identical number, for example six, and are disposed on straight lines concentric with the pins 37.

The slots are in particular disposed symmetrically in relation to the axis passing through the pins 37.

The notches 65 are designed to cooperate by catching with the two spindles 38 for the upper slots, and with the two spindles 36 for the lower slots, said slots being inclined in relation to the horizontal so that the blocks 21 and 24 move apart proportionally in relation to the spacing between the blocks 24 and 30, for example in a ratio of 1.1.3.

By pivoting the flanges forward or backward, the blocks are thus displaced vertically, guided by rails formed by the uprights 18 and the slots 19, between a position in which the three blocks are spaced apart to the maximum, and a position in which they are against one another.

FIG. 2a shows an alternative of the adjustment means according to the invention.

Here, the lateral flanges 62 comprise a rounded upper peripheral edge 200, equipped with six identical and uniformly distributed notches 201, corresponding to different sizes of femur.

A tilting component 202 is provided. It is movable in rotation about a horizontal axis 203 parallel to, and integral with, the main side of the upper block 30. More specifically, the component 202 is in the shape of an angle bracket whose upper wing is recessed except on the sides, thereby forming two lateral tabs 205 extending beyond the block 30, in the direction of the axis 203, said angle bracket extending over the entire length of the block, on the other side of said block from the position of the femur, the horizontal axis 203 being integral with the internal angle of said angle bracket which thus straddles the upper corner 204 of the block 30.

The lateral tabs 205 extending substantially in parallel and outward on each side of the upper face 206 of the block 30 are each terminated at their end by a lip 207 which is directed downward and is able to cooperate with the notches 201, the peripheral edge 200 of the flanges 62 extending below the upper face 206 of the block 30 in this embodiment.

The other wing 208 of the component 202 for its part extends downward.

It is designed to be pushed back toward the outside of the block 30 by pusher means, for example two helical springs 209 which are symmetrical in relation to the center of the wing, one side of which spring is integral with and bears on the block 30, and the other on the inner face of the wing 208.

The angle of the bracket is between 93 and 100°, for example 95°. When the operator, holding the blocks with one hand, presses with his fingers on the wing 208, counteracting the action of the springs, the lips 107 are moved away from the notches, and the flanges can pivot freely, moving the blocks apart or bringing them together.

Once the optimum spacing position has been obtained, corresponding, or corresponding substantially, to the size of the condyles of the patient, the pressure on the wing 208 is released.

By virtue of the spring, the wing 208 moves away from the block 30 by pivoting about the axis 203, thereby lowering the tabs 205 and the lips 207, which thus come to cooperate with the notches facing them.

FIGS. 3, 3A, 3B and 3C show a femoral cutting device 300 comprising four stainless steel blocks 301, 302, 303 and 304, which are movable in relation to the support element 305, namely a lower block 301, for the lower cut X, two median blocks 302 and 303 for the beveled anterior cut Y and for the beveled posterior cut Z, respectively, an upper block 304 for the anterior cut W.

The support element 305 includes a parallelepipedal platform 306 which comprises two rectangular transverse slits 307 which are parallel to the main faces of the platform and which pass right through the latter perpendicular to the direction 308 of the mutual movement of the blocks.

The support element includes two plates 309 which are movable in relation to the platform and are able to cooperate, with gentle friction, with the slits 307 and are connected to one another via a horizontal basepiece 310 which can be actuated manually by the practitioner, via a rod 311, between a position of total disengagement of the plates, and a position of maximum penetration of the plates, in which the basepiece 310 comes into abutment with the platform in such a way that the ends 312 of said plates emerge completely at the other side of the platform in order to constitute the lower base elements able to cooperate, in a bearing manner, with the femoral condyles.

The support element 305 furthermore includes two identical pairs of columns 313, which are cylindrical, for example, and disposed transversely in relation to the block 306, for very precise guiding and for lateral support of the blocks.

The columns are fixed at one end on the platform 306 and at the other end on an upper component 314.

Each block is drilled right through, and on either side, with two cylindrical bores 315, for the passage of the columns 313, in order to allow the blocks to slide with gentle friction along said columns.

More precisely, the lower 301 and upper 304 blocks each consist, for example, of a thick parallelepipedal plate equipped respectively with a slit 316 (317) passing transversely through the blocks, these being substantially parallel to the plates 309 and being designed to effect, respectively, a horizontal cut X in the lower part of the condyles, and a cut W which is slightly inclined in relation to the horizontal, called the anterior cut, in the upper part of the condyles of the femur.

The median blocks 302 and 303 have, for example, a cross section which is substantially in the shape of a rectangular trapezoid, the base of which is situated toward the outside of the device in relation to the bone and is parallel to the direction 308, and whose side directed toward the bone forms an angle of 45° in relation to the horizontal, symmetrically in relation to the central axis 318 parallel to the blocks.

The median blocks 302 and 303 each comprise a longitudinal slit, 319 and 320 respectively, passing transversely right through the blocks, from the bottom upward in the case of block 302, and from the top downward in the case of block 303, forming with one another an angle of 90° (twice 45°), and able to produce the cuts in the condyles called the beveled anterior cut Y, for slit 319, and beveled posterior cut Z, for slit 320.

More precisely, the median block is in a single piece, for example, and comprises a seat 321 for receiving the lower part of the pivot shaft symbolized at 322, and a recess 323 which will permit the guiding and passage of the intramedullary positioning rod (not shown).

The upper median block 303 for its part consists, for example, of two small identical blocks which are symmetrical and each equipped with a face 324, with semicylindrical recess, for guiding the shaft 322. It can also be in one piece.

The support element furthermore comprises two intermediate components 325 which are situated between the two median blocks, but not integral with said blocks, and are each equipped on their outer lateral face with an end spindle constituting the shaft 318 and forming the respective axes of the lateral flanges 326.

The intermediate components 325 comprise end parts 327 extending laterally beyond the device and designed to permit the device to be fixed on the femur by nails 328.

The flanges 326 are of the same type as those described with reference to FIG. 2a, that is to say they are equipped with notches 329 on the upper peripheral edges and designed to cooperate with the tilting component 330, for example identical to the tilting component 202 in said FIG. 2a.

More precisely, each lateral flange 326 is equipped with four slots in the shape of the arc of a curve, which slots are symmetrical in pairs in relation to the central shaft 318, namely two outer slots 331, each able to cooperate with a spindle respectively integral with the outer lateral wall of the lower and upper blocks, and two inner slots 332, each able to cooperate with a spindle respectively integral with the lateral wall of the lower and upper median blocks, the curved arcs of the slots 332 running in the opposite direction to the curved arcs 331.

Figure 3:
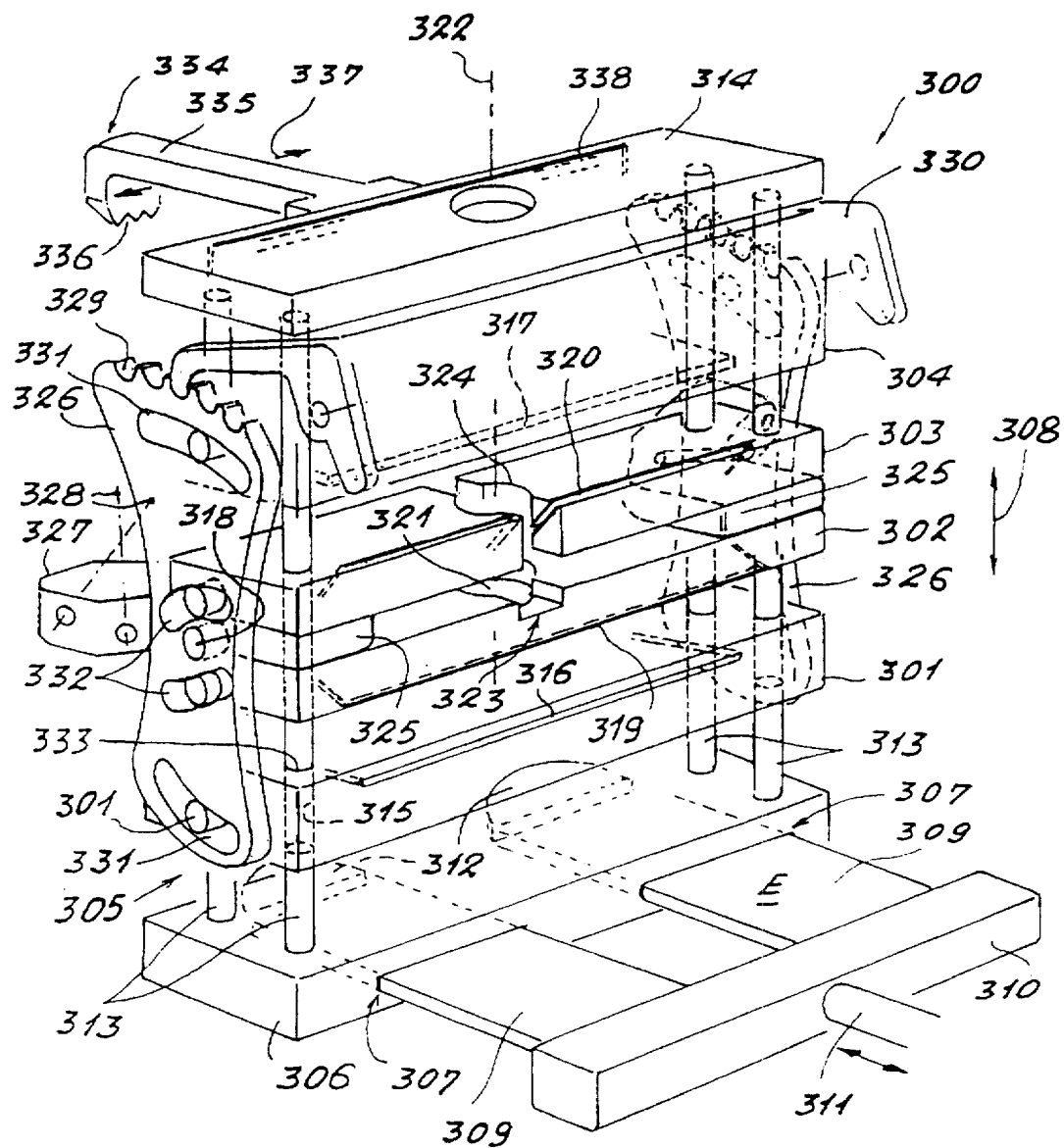
FIG. 3 is a diagrammatic perspective view of another embodiment of the device according to the invention.

In the embodiment in FIG. 3, the lower block 301 is movable and adjustable in height in relation to the platform 306 over a limited distance, which cannot exceed 2 cm, for example, by virtue of a mechanical limit stop 333 formed by an annular protuberance on one of the columns 313.

The tracer means 334 advantageously comprise a rod 335 to which a tracer blade 336 is rigidly fixed, the rod being mounted so that it is movable in the lateral direction 337 on a transverse rail 338 inside the component 314, thereby rendering the tracer means laterally adjustable in order to adapt to the femur in question.

Figure 3A:
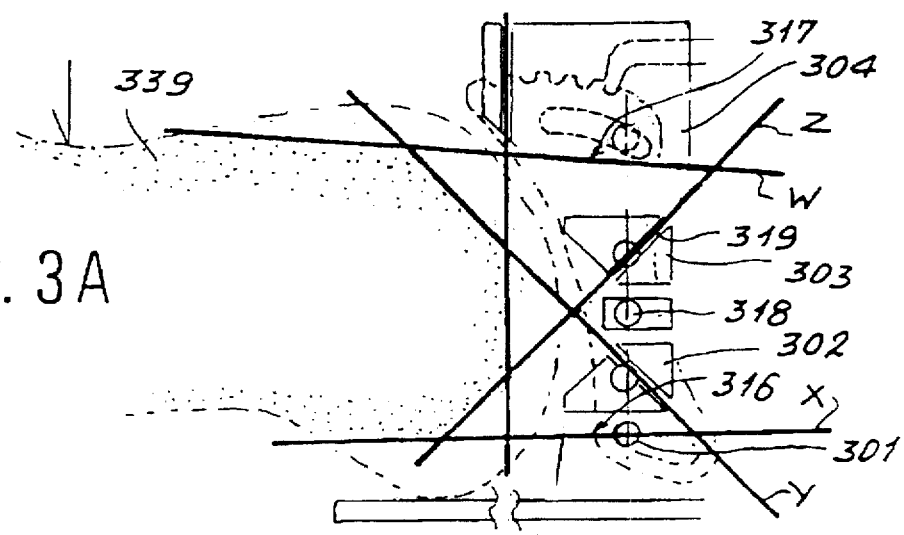
FIGS. 3A, 3B and 3C are diagrammatic cross sections showing the functioning and the cuts made by the device in FIG. 3, with femurs of different sizes.
Figure 3B:
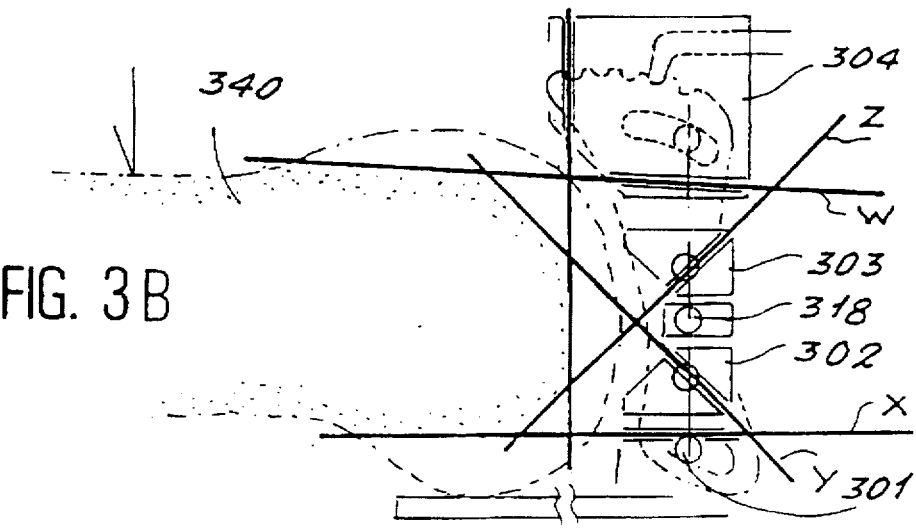
Figure 3C:
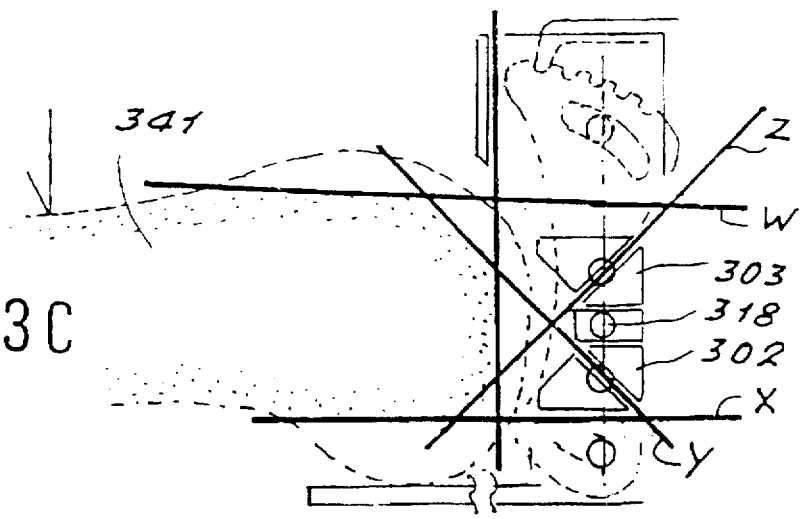

The functioning of the device according to the embodiment in FIG. 3 will now be described with reference to FIGS. 3A, 3B and 3C.

Each figure corresponds to a femur of different size, from biggest to smallest.

It will thus be seen that, by virtue of the invention, and on account of the proportional spacing between blocks, achieved automatically between the lower baseplate, whose position depends on the lower condyles, and the upper block, whose position is set by virtue of the tracer means, the cuts X, Y, Z and W are effected along lengths of bone which are not fixed, but which instead are adapted in a flexible and optimized manner to the femurs in question.

Thus, for a large femur 339, the distances between blocks 303 and 302 on the one hand, and between blocks 301 and 304 on the other hand, are increased, and then reduced (FIG. 3B, then FIG. 3C) as the dimensions of the femur 340 and 341 diminish, thereby adapting the lengths of horizontal cuts or substantially horizontal cuts (X and W), or cuts at 45° (Y, Z), to the femur in question.

Figure 4:
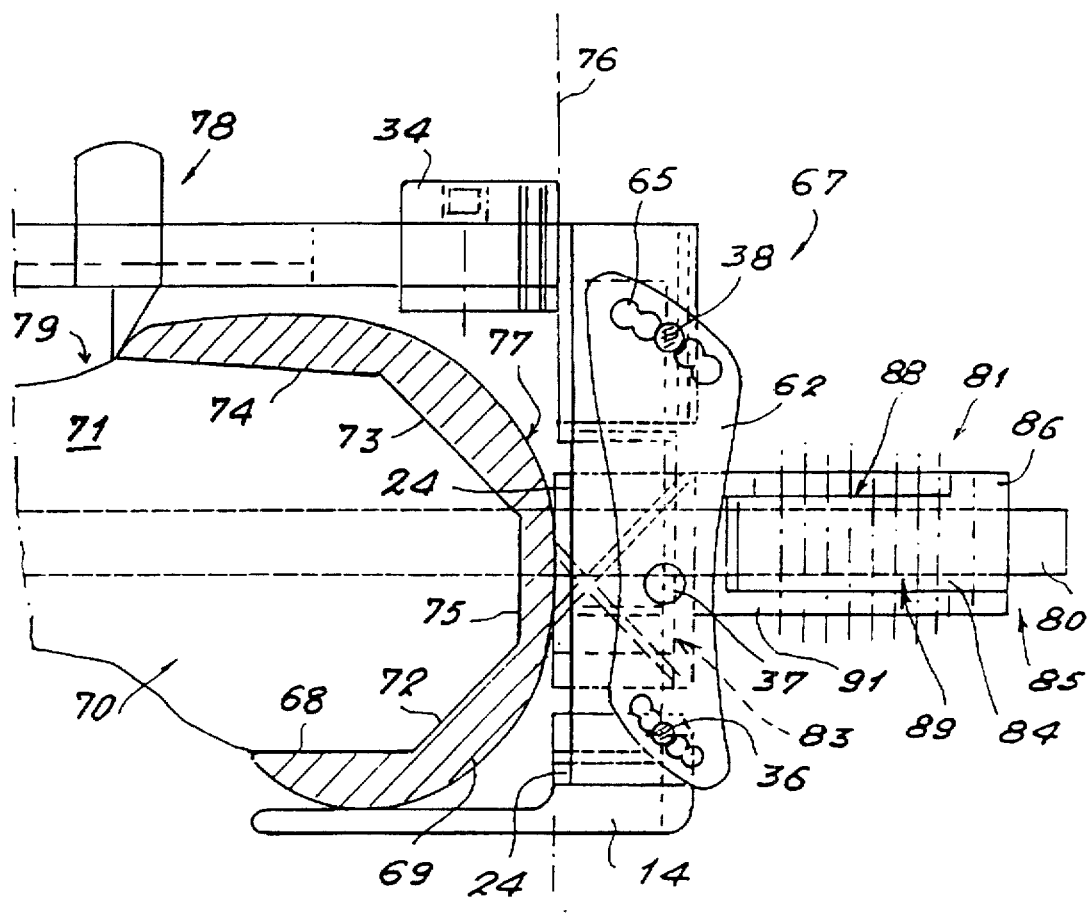
FIG. 4 is a side view of another embodiment of the femoral cutting device according to the invention.

FIG. 4 is a diagrammatic side view of a second embodiment of a femoral cutting device 67.

To simplify matters, in the descriptions which follow we will again use the same reference numbers as those in FIG. 2 to designate the same elements.

The device 67 comprises a support element 14, four cutting blocks, namely a lower block 21 for a posterior cut 68 of the condylar parts 69 at the end 70 of the femur 71, a central block 24 for a beveled posterior cut 72 and a beveled anterior cut 73, an upper block 30 for an anterior cut 74, and a block 34 for a distal cut 75, parallel to the common face 76 of the blocks 21, 24 and 30, which comes to bear on the outer face 77 of the condylar parts.

Tracer means 78 for the anterior cortical portion 79 of the femur are furthermore provided for adapting the device to the dimensions of the end 70 of the femur of the patient being treated.

The device 67 additionally comprises an intramedullary femoral rod 80 which is equipped at its end with a block 81 for adjusting the angle existing between said rod 80 on the one hand and the face 82 of the block on the other hand, which face is designed to be applied on, and coplanar with, the vertical outer face 83 of the central block 24.

Figure 4A:
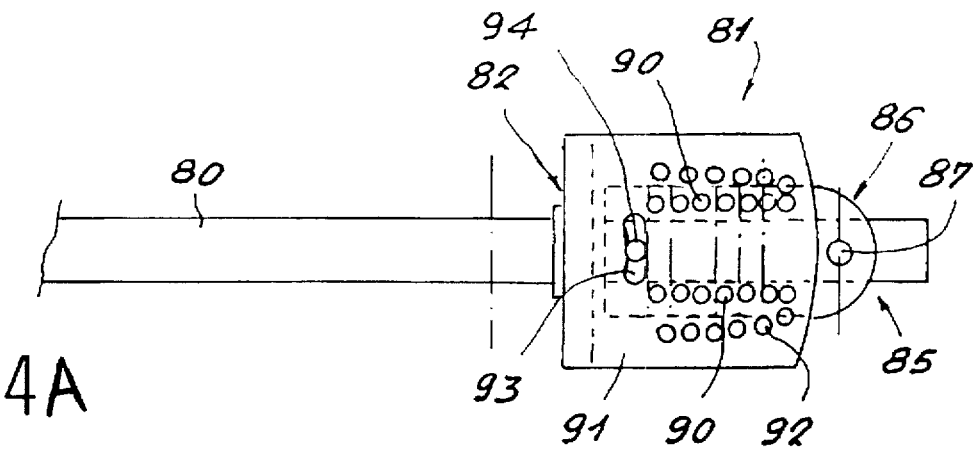
FIG. 4A is a plan view of that part of the device in FIG. 4 permitting the rotational adjustment of the femoral cutting guide in relation to the anatomical axis.
Figure 8:
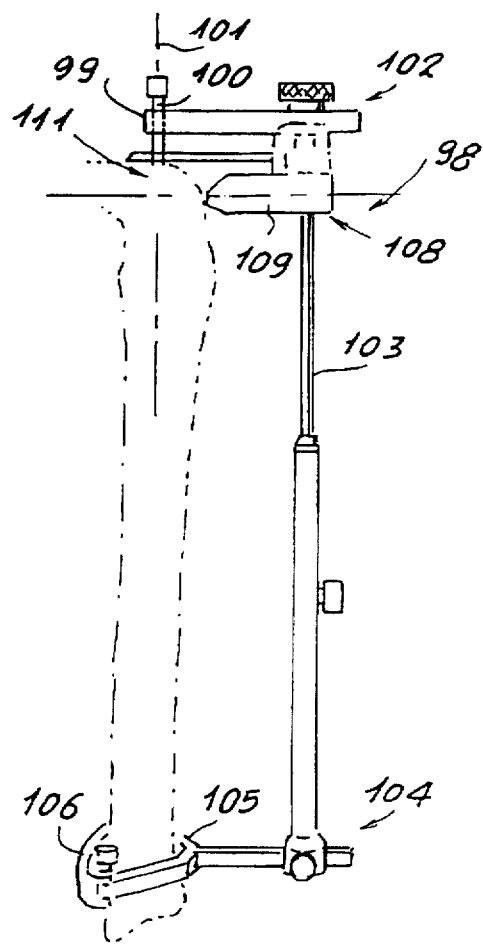
FIG. 8 is a side view of the tibial cutting device according to a first embodiment of the invention.
Figure 9:
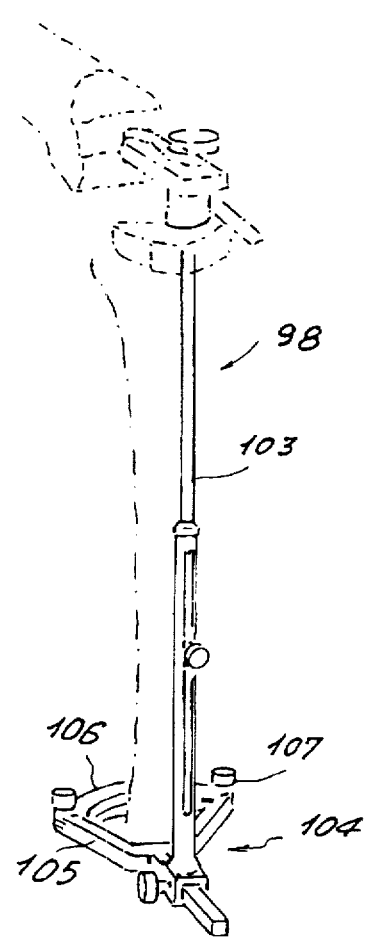
FIG. 9 is a diagrammatic perspective view of the device in FIG. 8.
Figure 10:
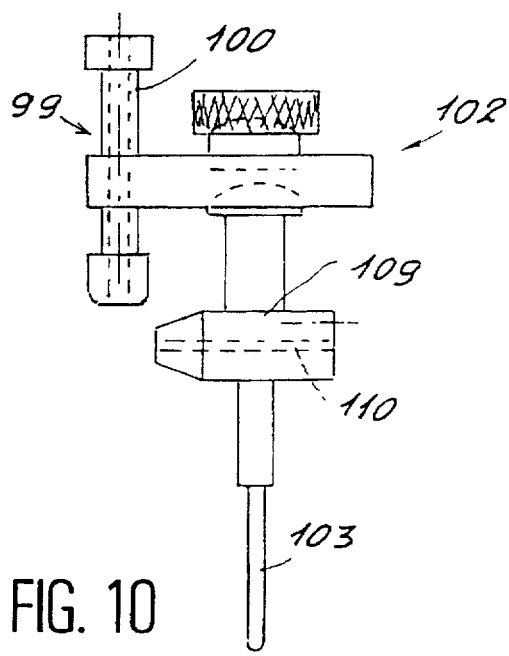
FIGS. 10 and 11 are side and plan views of the upper part of the device in FIGS. 8 and 9.
Figure 11:
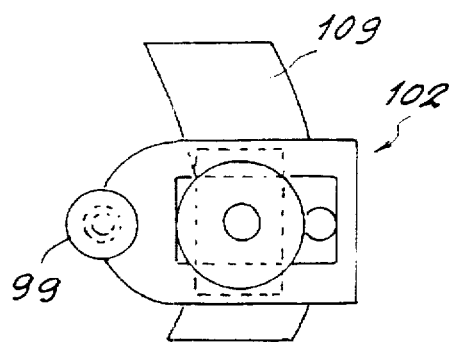

More precisely (see also FIG. 4A), the block 81 comprises a component 84 which is equipped with a longitudinal internal cylindrical bore which engages over the end 85 of the rod to which it is fixed via one end 86 by virtue of a key 87.

The component 84 comprises two plane surfaces 88 and 89, one upper and one lower respectively, toward its other end, these being drilled right through with a line of vertical holes 90 along, and parallel to, their two longitudinal peripheries, for example seven holes of small diameter, for example three millimeters.

The block 81 additionally comprises a second component 91 in the form of a jaw which presents a U-shaped cross section drilled with an axial and central bore for passage of the rod 80, the base of which component includes the vertical face 82 which is designed to be applied on the outer face 83 of the block 24, and the inner faces of the branches of the U cooperate frictionally with the plane faces 88 and 89.

The component 91 is such that it allows the face 82 to be pivoted in relation to the axis of the rod 80, on either side of the perpendicular position.

To do this, it comprises, on each longitudinal peripheral edge of the U-shaped jaw, a series of holes 92 which are disposed in succession along an arc of a circle of large diameter or along a straight line which is slightly inclined (2° to 3°) in relation to the axis of the bore of the U component, outside the holes 90 when the components 84 and 91 are in the same axis.

After the components 84 and 91 have been pivoted in relation to one another in order to render two holes 90 and 92 coaxial, a small pin (not shown) which is introduced into hole 90 and opposite hole 92 thereby permits a fixed positioning of the face 82 in relation to the rod 80 with a defined angle.

A slot 93 in the shape of an arc of a circle situated in a centered position in the upper branch of the component 91, and cooperating with a spindle 94 integral with the component 84 and with the rod 80, guides the component 91 in rotation about the axis of the key 87.

Another embodiment of the upper block 95 of the device according to the invention has been represented in FIGS. 5, 6 and 7.

In this case, the upper block is integral, in one piece, with the distal cutting block. It thus comprises, on the one hand, two vertical slits 96 for the distal cut, and, on the other hand, a substantially horizontal slit 97 for the anterior cut.

A rod 32, and orifices 43 and 44 as described hereinbefore, are also provided.

FIGS. 8, 9, 10 and 11 show an embodiment of the tibial cutting device 98 belonging to the apparatus according to the invention.

The apparatus 98 comprises a centering component 99 consisting of a cylindrical sleeve 100 for the passage of an intramedullary tibial rod 101, which is introduced in a manner known per se, the sleeve being fixed to an intermediate element 102 for supporting an outer rod 103.

The rod 103 comprises, in its lower part, means 104 which are adjustable in height, for fixing on the ankle, or in proximity thereto, by way of a V-shaped component 105 which is closed by a curved component 106 articulated at one end 107 and able to enclose the tibia in the closed position.

The upper part 108 of the rod 103 is integral with a tibial cutting block 109 which is equipped with a transverse slit 110 for cutting the condyles 111 of the tibial bone.

More precisely, and with reference to FIGS. 12 to 18, the intermediate element 102 comprises an openworked component 112 in the form of a portion of a cylinder which defines a slot 113 in which an assembly 114 integral with the end 115 of the outer rod 103 can be displaced.

The end sleeve 100 for passage of the intramedullary rod is fixed to one end of the component 112.

The assembly 114 includes, fixed and engaged on the end 115 of the rod, and in succession from the bottom upward:
  the cutting blade guide 109;
  a first wedge formed by a vertical cylinder 116 topped by a cap 117 whose upper face 118 is spherical or substantially spherical, of greater transverse dimensions than the width of the slot 113, and on which is fixed a rod 119 which is aligned axially with the cylinder 116 perpendicular to the face 118;
  the openworked component 112 placed in a movable manner about this rod;
  a second wedge 120 comprising a spherical or substantially spherical lower surface 120', of greater transverse dimensions than the width of the slot 113, designed to cooperate with the upper face 121 of the cylinder (the lower face 121' of which is able to cooperate with the upper face 118 of the first wedge); and
  a knurled screw 122 with which it is possible to tighten the components 117 and 120 on the openworked component, affording a determined inclination in the frontal plane and sagittal plane of the cutting guide 109, the geometric center 126 of the latter being the center or substantially the center of the radii of the walls 118, 120', 121 and 121'.

The cutting guide 109 furthermore comprises a slit 110 for passage of the cutting blade 123, and a movable tracer 124 for the upper surface of the condyle to be cut, said tracer being known per se.

A central orifice 125 for passage of the end 115 of the rod 103 is furthermore provided at the area of the geometric center 126 of the guide.

Orifices 127 for fixing the cutting guide on the tibia are also provided in a known manner.

Figure 12:
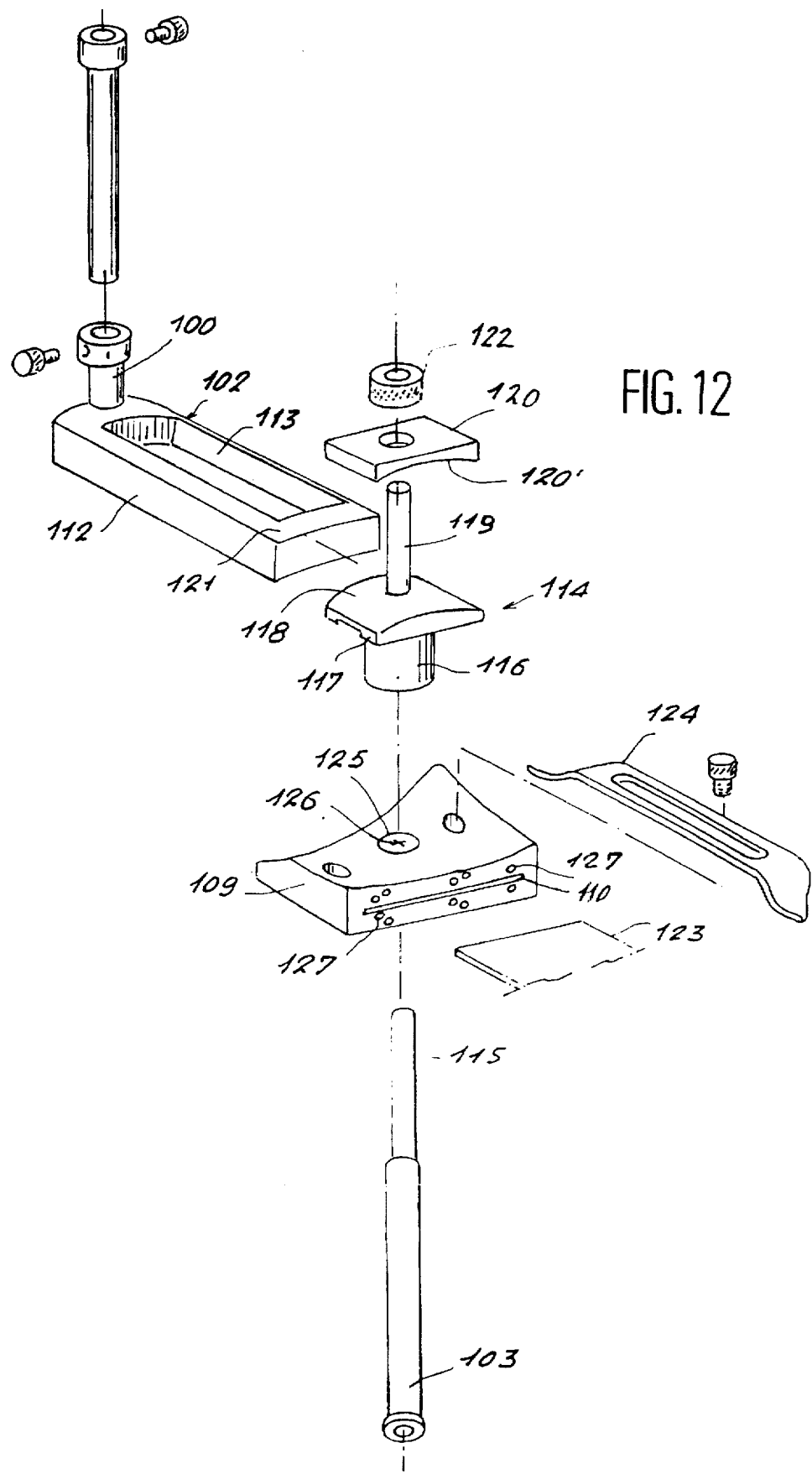
FIG. 12 is a perspective and exploded view of the upper part of an embodiment of the tibial cutting device similar to that described with reference to FIGS. 8 to 11.
Figure 13:
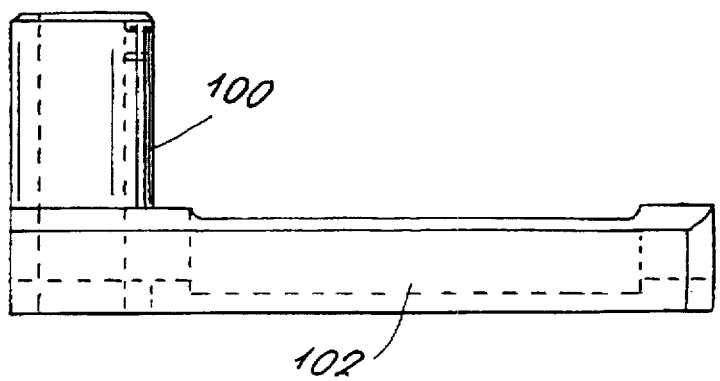
FIGS. 13, 14 and 15 are side, plan and front views, respectively, of the openworked component of the device in FIGS. 10 and 11.
Figure 14:
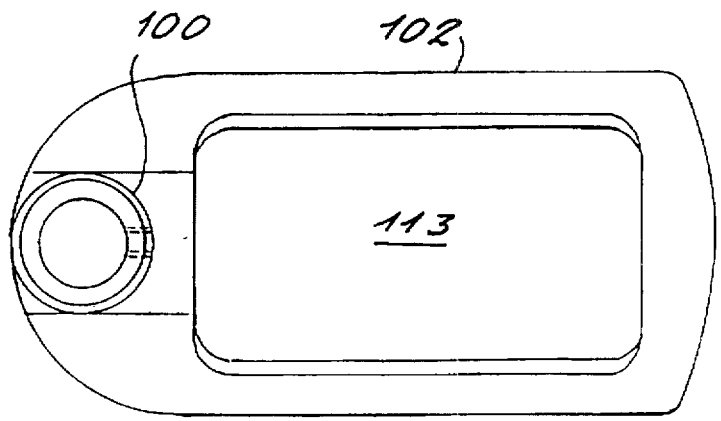
Figure 15:
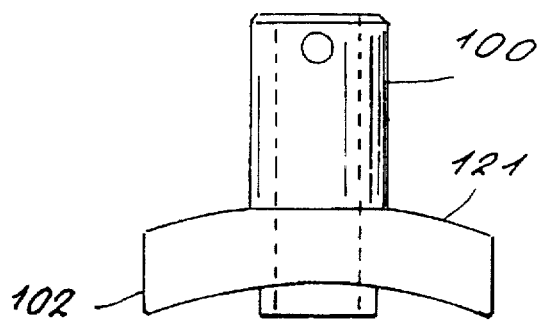
Figure 16:
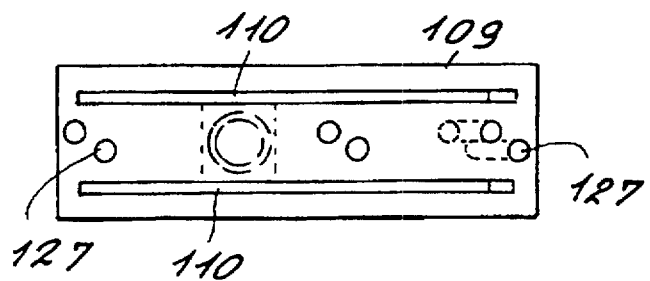
FIGS. 16, 17 and 18 are front, side and plan views, respectively, of the tibial cutting guide in FIGS. 10 and 11.
Figure 17:
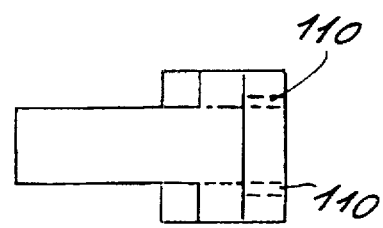
Figure 18:
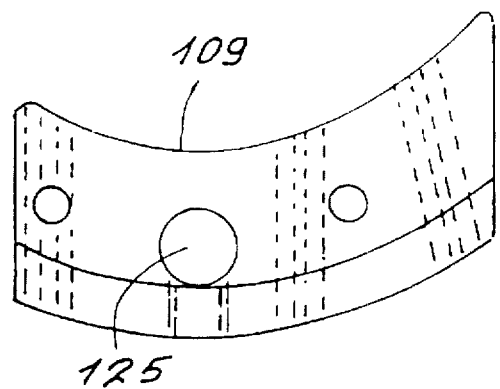

The positioning and the functioning of an apparatus for resection of the condyles of the knee according to the invention will now be described with reference being made more particularly to FIGS. 2 and 12.

After the knee has been opened by the surgeon, and with the knee flexed, the intramedullary rod 28 is put into place, the point of introduction being situated at the summit of the intercondylar notch, in the alignment of the femur, the subcartilaginous bone having been bored in advance with a drill, for example of diameter 6 mm.

The support element 14 is then put into place, bearing on the femoral condyles 13, by engaging on the rod 28 the guide 12 for the femoral cutting blades which is fixed to the support element 14, with which it is adjustable in height, until the plane of the coplanar faces of the blocks comes into contact with the condylar end.

The blade guide is then oriented in the sagittal plane by adjusting it in order to take account of the angle existing between the mechanical axis 1 of the lower limb and the anatomical axis 8 of the femur, by virtue of the adjustment system 42, the small pin 43 being introduced into the holes 48 and 49 facing each other, corresponding to the angle observed by the sighting means 50.

With the aid of the tracer means 56, 57, the block 30 for the anterior cut is additionally positioned at the necessary site, while adjusting the spacings between the cutting blade guides, as has been described, by pivoting the flanges 62 about the axis 66 in such a way as to space apart or bring together the blocks 21 and 30 in relation to the block 24, the spindles 38 and 36 being freely displaceable in the slots 64.

Said flanges are then brought to the blocks, the spindles then catching in the notches 65 of said slots, manually, or automatically via a spring return system (not shown).

The distances between the hole for passage of the spindle 37, passing through the axis 66, and the notches of two opposite slots situated on one and the same straight line passing through said hole, are in the same arithmetic ratio, the distance between the notches of the upper slot and the hole moreover decreasing from the top downward in proportions ranging from 1 to 0.7, for example.

Taking into account the arrangement of the slots, the spacing between the guide 21 for blades for the anterior cut and the guide 24 for blades for beveled anterior and beveled posterior cuts, on the one hand, and between said guide 24 for blades for beveled anterior and beveled posterior cuts and the guide 30 for the blade for the posterior cut, on the other hand, is thus adjustable in a proportional manner.

Once the guides have been perfectly positioned, the support element is fixed to the femur by lateral screws known per se, passing through fixation points (not shown) integral with the device, and the intramedullary rod is withdrawn.

In the case or [sic] the distal cutting block is movable in relation to the block 30, the transverse position of said distal cutting block is then adjusted, and it is fixed by tightening the knurled wheel 55.

The posterior, beveled posterior, beveled anterior, anterior and distal cuts are then produced at one and the same time, without modification of the adjustments and without removing pieces of bone between two cuts, which fact constitutes one of the advantages of the invention.

Before producing the femoral cuts, or thereafter, the bone of the tibia is also prepared for putting into place a tibial prosthesis which is able to cooperate with the femoral prosthesis intended to be fixed on the condylar part of the femoral bone which has been cut using the device hereinabove.

To do this, the intramedullary tibial rod 101 is moreover introduced into the tibia, and the positioning of a tibial cutting guide 109 is adjusted in the horizontal and sagittal plane, via an external correcting rod 103.

More precisely, a hole centered mediolaterally is drilled, the rod 101 is introduced into the centromedullary canal, the tracer 124 is placed bearing on the median portion of the healthy plateau of the condyle of the tibia, the component 102 is put into place, then the extramedullary rod is put into place, fixing it at a distance with the aid of the malleolar clamp 104 in such a way that the branch of the V or of the Y is aligned on the second metatarsal.

The alignment is then checked. In the frontal plane, the rod 103 must be in the continuation of the second metatarsal distally and in line with the inner edge of the tibial tuberosity proximally.

In the sagittal plane, the rod is parallel to the mechanical axis of the tibia and not to the tibial crest.

The cutting level is then determined by virtue of the tracer 124 comprising a plate with a toothed edge, the cutting guide being displaced in rotation about its geometric center, by unscrewing the knurled wheel 122, and orientation of the guide by pivoting surfaces 120, 120', 118 and 121 against one another.

The support element is then fixed to the femur by lateral screws in a manner known per se, and the intramedullary rod is withdrawn. The tibial cut is then made.

The whole of the apparatus is then withdrawn, the femur and tibia of the patient being ready for prostheses to be put into place.

The present invention is not limited to the embodiments which have been described more specifically herein. Instead, it encompasses all variants thereof, and in particular those where:

the support component 14 includes two lateral uprights, for example cylindrical, designed to cooperate with corresponding orifices drilled on each side in the blocks 21, 24 and 30, in order to guide said blocks and hold them in place.

We claim:

1. An apparatus for resection of condyles of a knee for putting a prosthesis into place, comprising a femoral cutting devices, including said femoral cutting device comprising:

a support element equipped with a lower baseplate able to cooperate, in a bearing manner, with femoral condyles;

a guide for blades for femoral cuts, being anterior cut, beveled anterior cut, beveled posterior cut, posterior cut, and distal cut, said guide being fixed and comprising at least three blocks, of which at least two blocks are movable in relation to said support element, said blocks being adjustable in height in relation to one another, one of the blocks comprising means for guiding at least one cut from among the anterior cut, the posterior cut, the beveled anterior cut, and the beveled posterior cut, and the other blocks comprising means for guiding remaining cuts from among the anterior cut, the posterior cut, the beveled anterior cut, and the beveled posterior cut;

an intramedullary femoral rod for orienting and centering of said device; and means for tracing an anterior cortical portion of the femur, said tracing means being integral with said guide.

2. The apparatus according to claim 1, wherein the three blocks are movable in relation to said support element and comprise a lower block for the posterior cut, a central block for the beveled anterior and beveled posterior cuts, and an upper block for the anterior cut.

3. The apparatus according to claim 2, wherein the lower block is adjustable in height in relation to the lower baseplate by a distance not larger than a defined value.

4. The apparatus according to claim 1, wherein the cutting blade guide includes four blocks which are movable in relation to said support element, the blocks being a lower block for the posterior cut, two median blocks comprising a first block for the beveled anterior cut and a second block for the beveled posterior cut, and an upper block for the anterior cut.

5. The apparatus according to claim 1, wherein the device includes means for adjusting spacings between blocks in a proportional manner.

6. The apparatus according to claim 5, wherein the adjusting means comprises two lateral flanges which are disposed on either side of the blocks and are movable in rotation about a central shaft between first and second positions, at the first position the blocks being spaced apart to a maximum from one another, and at the second position the blocks being brought together, said lateral flanges being equipped with slots in a shape of an arc of a circle, which are disposed symmetrically in relation to said shaft and are able to cooperate with spindles which are integral with outer lateral walls of the mutually movable blocks.

7. The apparatus according to claim 6, wherein the three blocks are movable in relation to said support element and comprise a lower block for the posterior cut, a central block for the beveled anterior and beveled posterior cuts, and an upper block for the anterior cut, and wherein the cutting blade guide including a central block for the beveled cuts, the central shaft is integral with said central block, and the lateral flanges are each equipped with two slots in the shape of an arc of a circle, which are symmetrical in relation to said central shaft and are able to cooperate with spindles respectively integral with the lateral walls of the lower and upper blocks.

8. The apparatus according to claim 6, wherein the cutting blade guide includes four blocks, which are movable in relation to said support element, being a lower block for the posterior cut, two median blocks comprising a first block for the beveled anterior cut and a second block for the beveled posterior cut, and an upper for anterior cut, and wherein the cutting blade guide including two median blocks, the central shaft is integral with at least one intermediate element disposed between the two median blocks, and the lateral flanges are each equipped with four slots in the shape of an arc of a circle and symmetrical in pairs in relation to said central shaft, being two outer slots able to cooperate with spindles respectively integral with the lateral walls of the lower and upper blocks, and two inner slots able to cooperate with spindles respectively integral with the integral walls of the median blocks.

9. The apparatus according to claim 6, wherein an upper edge of the lateral flanges is curved and notched, the adjustment means comprising a tilting component in a form of an angle bracket straddling, and movable in rotation about, a shaft integral with an outer ridge of the upper block, including two lateral end parts whose respective peripheral edges are equipped with a peripheral lip which is able to cooperate with notches, said angle bracket being movable between a compressed position, in which the lips are freed from the notches, and a spring-return position, in which the lips are caught in said notches.

10. The apparatus according to claim 2, wherein the support element includes two pairs of columns which guide the blocks, connected to one another by end-pieces and situated on either side of the apparatus, said blocks comprising bores for a passage of said columns in order to allow said blocks to slide with gentle friction along said columns between the two said positions.

11. The apparatus according to claim 1, wherein the lower baseplate of the support element comprises at least one movable plate which is able to cooperate, in a bearing manner, with the femoral condyles.

12. The apparatus according to claim 1, wherein the means for tracing an anterior cortical portion of the femur can be displaced laterally in relation to the support element.

13. The apparatus according to claim 1, wherein the femoral cutting device includes means for adjusting an angle formed between an axis perpendicular to the cutting blade guide and the intramedullary rod.

14. The apparatus according to claim 13, wherein the means for adjusting the angle are integral with the femoral intramedullary rod.

15. The apparatus according to claim 13, wherein the means for adjusting the angle are integral with an upper block.

16. The apparatus according to claim 1, wherein the cutting blade guide includes a distal cutting block integral with an anterior cutting block and equipped with at least two slits for guiding distal cutting blades.

17. The apparatus according to claim 1, further comprising a tibial cutting device equipped with a centering component which is able to cooperate with a tibial intramedullary rod, said tibial cutting device including a rod external to tibia, one end of which rod is integral with said component and includes a cutting block equipped with a curved surface for contact with the tibia, and the other end of which rod is designed to be fixed temporarily on a portion of the tibia, wherein said end of the rod external to the tibia and integral with the centering component is fixed to said component via an intermediate element designed to permit an adjustment of a position of the tibial cutting block in a frontal plane and in a sagittal plane, by pivoting about a center coinciding, or substantially with the center of gravity of said tibial cutting guide.

18. The apparatus according to claim 17, wherein the intermediate element comprises an open-worked component in a form of a cylindrical tube portion defining a slot in which the end of the external rod can be displaced, said end being equipped with two substantially hemispherical wedges situated on either side of said component, said wedges being able to cooperate frictionally and to be held pressed against inner and outer cylindrical surfaces of said component by clamping means, a center of the hemispherical wedges and an axis of a cylinder passing through substantially the center, of gravity of said cutting block.

\* \* \* \* \*

UNITED STATES PATENT AND TRADEMARK OFFICE
CERTIFICATE OF CORRECTION

PATENT NO. : 5,749,876
DATED : MAY 12, 1998
INVENTOR(S) : DUVILLIER ET AL.

It is certified that error appears in the above-identified patent and that said Letters Patent is hereby corrected as shown below:

Title page, [87] PCT Pub. Date: "July 25, 1996" should read —January 25, 1996—

Col. 1, line 43: "90°" should read —9°—

Col. 6, line 29: "30°" should read —3°—

Col. 14, line 4, claim 1: "devices" should read —device—

Col. 15, line 25, claim 10: "claim 2" should read —claim 5—

Signed and Sealed this

Seventh Day of December, 1999

Attest:

Q. TODD DICKINSON

*Attesting Officer*  *Acting Commissioner of Patents and Trademarks*